United States Patent [19]

Berg et al.

[11] Patent Number: 4,676,874
[45] Date of Patent: Jun. 30, 1987

[54] SEPARATION OF N-PROPYL ACETATE FROM N-PROPANOL AND WATER BY EXTRACTIVE DISTILLATION

[76] Inventors: Lloyd Berg, 1314 S. 3rd Ave.; An-I Yeh, 709 S. 12th Ave., both of Bozeman, Mont. 59715

[21] Appl. No.: 795,866

[22] Filed: Nov. 7, 1985

[51] Int. Cl.[4] .......................... B01D 3/40; C07C 67/54
[52] U.S. Cl. ........................................ 203/51; 203/56; 203/58; 203/59; 203/64; 560/248
[58] Field of Search ....................... 203/58, 59, 64, 63, 203/51, 56, 62, 18, 19, 14; 560/248, 234; 568/913, 916, 918

[56] References Cited

U.S. PATENT DOCUMENTS

| | | | |
|---|---|---|---|
| 1,770,414 | 7/1930 | Martin et al. | 560/234 |
| 4,507,176 | 3/1985 | Berg et al. | 203/58 |
| 4,592,805 | 6/1986 | Berg et al. | 203/60 |

FOREIGN PATENT DOCUMENTS

| | | | |
|---|---|---|---|
| 1089744 | 9/1960 | Fed. Rep. of Germany | 203/64 |
| 46701 | 4/1979 | Japan | 560/248 |

*Primary Examiner*—Wilbur Bascomb

[57] ABSTRACT n-Propyl acetate cannot be completely removed from n-propyl acetate - n-propanol - water mixtures by distillation because of the presence of the minimum ternary azeotrope. n-Propyl acetate can be readily removed from mixtures containing it, n-propanol and water by using extractive distillation in which the extractive distillation agent is a higher boiling oxygenated or nitrogenous organic compound or a mixture of these. Typical examples of effective agents are N-methylpyrrolidone; triethanolamine; N-methylpyrrolidone and ethylene glycol.

2 Claims, No Drawings

SEPARATION OF N-PROPYL ACETATE FROM N-PROPANOL AND WATER BY EXTRACTIVE DISTILLATION

FIELD OF THE INVENTION

This invention relates to a method for separating n-propyl acetate from n-propanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

One of the conmercially important ways to manufacture n-propyl acetate is by the catalytic esterification of n-propanol with aectic acid. n-Propyl acetatc (b.p.=101.6° C.), n-propanol (b.p.=97.2° C.) and water (b.p.=100° C.) form a ternary azeotrope boiling at 82.2° C. and containing 59.5 weight percent n-propyl acetate, 19.5 wt. % n-propanol and 21 wt. % water. n-Propyl acetate also forms a binary azeotrope with n-propanol which boils at 94° C. and contains 37 wt. % n-propyl acetate, and a binary azeotrope with water boiling at 82.4° C. and containing 86 wt. % n-propyl acetate. n-Propanol also forms a binary minimum azeotrope with water which boils at 88.1° C. and contains 71.8 wt. % n-propanol. Thus in the esterification of n-propanol with acetic acid to form n-propyl acetate and water, the rectification of this mixture has three binary and a ternary azeotrope to contend with, and yields the lowest boiling constituent, namely the n-propyl acetate - n-propanol - water ternary azeotrope. It is therefore impossible to produce n-propyl acetate from n-propanol and water mixtures by rectification because the lower boiling ternary azeotrope will always come off overhead as the initial product. Any mixture of n-propyl acetate, n-propanol and water subjected to rectification at one atmosphere pressure will produce an overhead product boiling at 82.2° C. and containing 59.5 wt. % n-propyl acetate, 19.5 wt. % n-propanol and 21 wt. % water. Extractive distillation would be an attractive method of effecting the separation of n-propyl acetate from n-propanol if agents can be found that (1) will break the n-propyl acetate-n-propanol - water azeotrope and (2) are easy to recover from the n-propanol, that is, form no azeotrope with n-propanol and boil sufficiently above n-propanol to make the separation by rectification possible with only a few theoretical plates.

Extractive distillation typically requires the addition of an equal amount to twice as much extractive agent as the n-propyl acetate-n-propanol - water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation.

Another consideration in the selection of the extractive distillation agent is its recovery from the bottoms product. The usual method is by rectification in another column. In order to keep the cost of this operation to a minimum, an appreiable boiling point difference between the compound being separated and the extractive agent is desirable. It is also desirable that the extractive agent be miseible with n-propanol otherwise it will form a two-phase azeotrope with the n-propanol in the recovery column and some other method of separation will have to be employed.

The breaking of this azeotrope by extractive distillation is a new concept. The closest application of the concept might be the breaking of the methyl acetate - methanol described by Berg & Yeh, CHEMICAL ENGINEERING COMMUNICATIONS, p.3219–3223, 1984.

OBJECTIVE OF THE INVENTION

The object of this invention is to provide a process or method of extractive distillation that will enhance the relative volatility of n-propyl acetate from n-propanol in their separation in a rectification column. It is a further object of this invention to identify suitable extractive distillation agents which will eliminate the n-propyl acetate - n-propanol - water ternary azeotrope and make possible the production of pure n-propyl acetate and n-propanol by rectification. It is a further object of this invention to identify organic compounds which, in addition to the above constraints, are stable, can be separated from n-propanol by rectification with relatively few theoretical plates and can be recycled to the extractive distillation column and reused with little decomposition.

SUMMARY OF THE INVENTION

The objects of the invention are provided by a process for separating n-propyl acetate from n-propanol which entails the use of certain oxygenated, nitrogenous and/or sulfur containing organic compounds as the agent in extractive distillation.

DETAILED DESCRIPTION OF THE INVENTION

We have discovered that certain oxgenated and nitrogenous organic compounds, some individually but principally as mixtures, will effectively negate the n-propyl acetate - n-propanol - water ternary azeotrope and permit the separation of pure n-propyl acetate from n-propanol by rectification when employed as the agent in extractive distillation. Table 1 lists the compounds, mixtures and approximate proportions that we have found to be effective. The data in Table 1 was obtained in a vapor-liquid equilibrium still. In each case, the starting material was the n-propyl acetate - n-propanol - water azeotrope. The ratios are the parts by weight of extractive agent used per part of n-propyl acetate - n-propanol - water azeotrope. The relative volatilities are listed for each of the two ratios employed. The compounds that are effective when used alone are triethanolamine and N-methylpyrrolidone. The compounds which are effective when used in mixtures of two compounds are ethylene glycol, 1,6-hexanediol and tetraethylene glycol. The two relative volatilities shown in Table 1 correspond to the two different ratios employed. For example, in Table 1, one part of triethanolamine with one part of of the n-propyl acetate-n-propanol - water azeotrope gives a relative volatility of 1.44, 6/5 parts of triethanolamine give 1.54. One half part of N-methylpyrrolidone mixed with one half part of ethylene glycol with one part of the n-propyl acetate - n-propanol - water azeotrope gives a relative volatility of 1.69, 3/5 parts of N-methylpyrrolidone plus 3/5 parts of ethylene glycol gives 1.91. In every example in Table 1, the starting material is the n-propyl acetate - n-propanol - water azeotrope which possesses a relative volatility of 1.00.

TABLE 1
Extractive Distillation Agents That Are Effective In Separating n-Propyl Acetate From n-Propanol

| Compounds | Ratios | | Relative Volatilities | |
|---|---|---|---|---|
| Triethanolamine | 1 | 6/5 | 1.44 | 1.54 |
| N—Methylpyrrolidone | " | — | 1.54 | |
| N—Methylpyrrolidone, Ethylene glycol | $(1/2)^2$ | $(3/5)^2$ | 1.69 | 1.91 |
| N—Methylpyrrolidone, 1,6-Hexanediol | " | " | 1.17 | 1.18 |
| N—Methylpyrrolidone, Tetra-ethylene glycol | " | " | 1.24 | 1.16 |
| N—Methylpyrrolidone, Triethanolamine | " | " | 1.42 | 1.58 |

TABLE 2
Data From Runs Made In Rectification Column

| Agents | Wt. % n-Propyl Acetate | | Relative Volatility |
|---|---|---|---|
| | Overhead | Bottoms | |
| Triethanolamine | 94.1 | 67.3 | 1.55 |
| N—Methylpyrrolidone, Ethylene glycol 1:1 | 91.3 | 44.1 | 1.78 |

Notes:
Compositions are reported on agent- and water-free basis
Agents added at 20 ml/min. & 50° C.
Ratio of mixed agents is by weight Several of the compounds and mixtures listed in Table 1 and whose relative volatility had been determined in the vapor-liquid equilibrium still, were then evaluated in a glass perforated plate rectification column possessing 4.5 theoretical plates. The n-propyl acetate-n-propanol - water mixture studied contained 59.5 wt. % n-propyl acetate, 19.5 wt. % n-propanol and 21 wt. % water which is the ternary azeotrope composition. In every case the ratio of n-propyl acetate to n-propanol in the overhead is greater than 3.05 and the results are tabulated in Table 2. Without the extractive agent, the overhead would be the azeotrope whose ratio of n-propyl acetate to n-propanol is 3.05. This proves that the extractive agent is negating the azeotrope and makes the rectification proceed as if the azeotrope no longer existed and brings the more volatile components, n-propyl acetate and water, out as overhead products. It is our belief that this is the first time that this has been accomplished for this azeotrope.

The data in Table 2 was obtained in the following manner. The charge was 59.5% n-propyl acetate, 19.5% n-propanol and 21% water and after a half hour of operation in the 4.5 theoretical plate column to establish equilibrium, triethanolamine at 50° C. and 20 ml/min. was pumped in. The rectification was continued for about two hours with sampling of overhead and bottoms after one hour, 1.5 hours and two hours. The average of the three analyses is shown in Table 2 and was 94.1% n-propyl acetate in the overhead and 67.3% in the bottoms, both on a water-free basis which gives a relative volatility of 1.55 of n-propyl acetate to n-propanol.

This indicates that the ternary azeotrope has been negated and separation accomplished. The n-propyl acetate comes off in the form of its binary azeotrope with water which on condensation, immediately forms two layers. The solubility of n-propyl acetate in liquid water is only 1.6%.

THE USEFULNESS OF THE INVENTION

The usefulness or utility of this invention can be demonstrated by referring to the data presented in Tables 1 and 2. All of the successful extractive distillation agents show that n-propyl acetate, n-propanol and water can be separated from their ternary azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity n-propyl acetate from any mixture of these three including the ternary minimum azeotrope. The stability of the compounds used and the boiling point difference is such that complete recovery and recycle is obtainable by a simple distillation and the amount required for make-up is small.

WORKING EXAMPLES

EXAMPLE 1

The n-propyl acetate - n-propanol - water azeotrope is 59.5 wt. % n-propl acetate, 19.5 wt. % n-propanol and 21 wt % water. Fifty grams of the n-propyl acetate - n-propanol - water azeotrope and fifty grams of triethanolamine were charged to an Othmer type glass vapor-liquid equilibrium still and refluxed for eleven hours. Analysis of the vapor and liquid by gas chromatography gave a vapor composition of 74.1% n-propyl acetate, 25.9% n-propanol; a liquid composition of 66.5% n-propyl acetate, 33.5% n-propanol. This indicates a relative volatility of 1.44. Ten grams of triethanolamine were added and refluxing continued for another twelve hours. Analysis indicated a vapor composition of 71.1% n-propyl acetate, 28.9% n-propanol; a liquid composition of 61.5% n-propyl acetate, 38.5% n-propanol which is a relative volatility of 1.54.

EXAMPLE 2

Fifty grams of the n-propyl acetate - n-propanol - water azeotrope, 25 grams of N-methylpyrrolidone and 25 grams of ethylene glycol were charged to the vapor-liquid equilibrium still and refluxed for seven hours. Analysis indicated a vapor composition of 73% n-propyl acetate, 27% n-propanol; a liquid composition of 61.6% n-propyl acetate, 38.4% n-propanol which is a relative volatility of 1.69. Five grams of N-methylpyrrolidone and five grams of ethylene glycol were added and refluxing continued for another two hours. Analysis indicated a vapor composition of 73.5% n-propyl acetate, 26.5% n-propanol; a liquid composition of 59.2% n-propyl acetate, 40.8% n-propanol which is a relative volatility of 1.91.

EXAMPLE 3

A glass perforated plate rectification column was calibrated with ethylbenzene and p-xylene which possesses a relative volatility of 1.06 and found to have 4.5 theoretical plates. A solution comprising 268 grams of n-propyl acetate, 88 grams of n-propanol and 94 grams of water was placed in the stillpot and heated. When refluxing began, an extractive agent consisting of pure triethanolamine was pumped into the column at a rate of 20 ml/min. The temperature of the extractive agent as it entered the column was 50° C. After establishing the feed rate of the extractive agent, the heat input to the n-propyl acetate, n-propanol and water in the stillpot was adjusted to give a total reflux rate of 10-20 ml/min. After one hour of operation, the overhead and bottoms samples of approximately two ml. were collected and analysed using gas chromatography. The overhead analysis was 94.1% n-propyl acetate, 5.9% n-propanol. The bottoms analysis was 67.3% n-propyl acetate, 32.7% n-propanol. Using these compositions in the Fenske equation, with the number of theoretical plates in the column being 4.5, gave an average relative volatility of 1.57 for each theoretical plate. After 1½ hours of total operating time, the overhead and bottoms samples were again taken and analysed. The overhead composition was 95.5% n-propyl acetate, 4.5% n-propanol and the bottoms composition was 69% n-propyl acetate, 31% n-propanol. This gave an average relative volatility of 1.58 for each theoretical plate. After two hours of total operating time, the overhead and bottoms samples were again taken and analysed. The overhead composition was 95.7% n-propyl acetate, 4.3% n-propanol and the bottoms composition was 74.8% n-propyl acetate, 25.2% n-propanol. This gave an average relative volatility of 1.57 for each theoretical plate.

EXAMPLE 4

A solution of 268 grams of n-propyl acetate, 88 grams of n-propanol and 94 grams of water was placed in the stillpot of the same column used in Example 3 and heat applied. When refluxing began, an extractive agent comprising 50% N-methylpyrrolidone and 50% ethylene glycol was fed into the top of the column at a feed rate of 20 ml/min. and a temperature of 50° C. After establishing the feed rate of the extractive agent, the heat input to the n-propyl acetate, n-propanol and water in the stillpot was adjusted to give a total reflux rate of 10-20 ml/min. Having established the reflux rate, the column was allowed to operate for one hour. After one hour of steady operation, overhead and bottoms samples of approximately two ml. were collected and analysed using gas chromatography. The overhead composition was 91.3% n-propyl acetate, 8.7% n-propanol, the bottoms composition was 44.1% n-propyl acetate, 55.9% n-propanol. Using these compositions in the Fenske equation with the number of theoretical plates in the column being 4.5, gave an average relative volatility of 1.78 for each theoretical plate. After 1½ hours of total operation, the overhead composition was 92% n-propyl acetate, 8% n-propanol and the bottoms composition was 47.5% n-propyl acetate, 52.5% n-propanol. This gave an average relative volatility of 1.76 for each theoretical plate. After two hours of total operation, the overhead composition was 92.2% n-propyl acetate, 7.8% n-propanol and the bottoms composition was 46.5% n-propyl acetate, 53.5% n-propanol. This gave an average relative volatility of 1.79 for each theoretical plate.

The nature of the present invention having been described, what we wish to claim as new and useful and secure by Letters Patent is:

1. A method for recovering n-propyl acetate from a mixture of n-propyl acetate, n-propanol and water which comprises distilling a mixture of n-propyl acetate, n-propanol and water in a rectification column in the presence of about one part of extractive agent per part of n-propyl acetate - n-propanol - water mixture, recovering n-propyl acetate and water as overhead product and obtaining the extractive agent and n-propanol from the stillpot, the extractive agent comprises at least N-methylpyrrolidone.

2. The method of claim 1 in which the extractive agent comprises a mixture of N-methylpyrrolidone and at least one material from the group consisting of ethylene glycol, 1,6-hexanediol, tetraethylene glycol and triethanolamine.

* * * * *